United States Patent
Ten Kate et al.

(10) Patent No.: US 8,408,041 B2
(45) Date of Patent: Apr. 2, 2013

(54) FALL DETECTION SYSTEM

(75) Inventors: Warner Ten Kate, Eindhoven (NL); Ingrid Christina Maria Flinsenberg, Eindhoven (NL); Ningjiang Chen, Shanghai (CN); Sheng Kim, Shanghai (CN); Stephan Schlumbohm, Aachen (DE); Rudie Bernardus Maria Schonenberg, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 728 days.

(21) Appl. No.: 12/596,449

(22) PCT Filed: Apr. 15, 2008

(86) PCT No.: PCT/IB2008/051424
§ 371 (c)(1),
(2), (4) Date: Oct. 19, 2009

(87) PCT Pub. No.: WO2008/129451
PCT Pub. Date: Oct. 30, 2008

(65) Prior Publication Data
US 2010/0121226 A1 May 13, 2010

(30) Foreign Application Priority Data
Apr. 19, 2007 (CN) .......................... 2007 1 0096643

(51) Int. Cl.
*G01N 3/00* (2006.01)
*G01N 19/02* (2006.01)

(52) U.S. Cl. ...................... 73/12.06; 73/12.01; 73/12.04; 600/587; 600/595

(58) Field of Classification Search ................. 73/12.01, 73/12.04, 12.06; 701/141, 150, 151; 600/595
See application file for complete search history.

(56) References Cited

U.S. PATENT DOCUMENTS

| | | | |
|---|---|---|---|
| 5,836,887 A * | 11/1998 | Oka et al. ...................... | 600/494 |
| 6,547,728 B1 | 4/2003 | Cornuejols | |
| 2005/0027216 A1* | 2/2005 | Guillemaud et al. ......... | 600/595 |
| 2005/0033200 A1 | 2/2005 | Soehren et al. | |

FOREIGN PATENT DOCUMENTS

| | | |
|---|---|---|
| EP | 0816986 A2 | 1/1998 |
| EP | 1422577 A2 | 5/2004 |
| EP | 1493385 A1 | 1/2005 |
| GB | 2401466 A | 11/2004 |

* cited by examiner

*Primary Examiner* — Lisa Caputo
*Assistant Examiner* — Roger Hernandez-Prewitt

(57) ABSTRACT

The invention relates to a fall detection system, for detecting human fall incidents. The detection system comprises a sensor module to be worn by a user, for collecting motion data of his body, for instance acceleration data; first evaluation logic for identifying a potential fall incident on the basis of an impact observed in the acceleration data; and second evaluation logic for verifying that the sensor module is actually worn by the user, at least around the time of said impact, to prevent the system from raising an alarm if only the sensor module has fallen. The second evaluation logic may comprise free fall detection means for evaluating the acceleration data on characteristics which are typical for a free falling object, such as one or more full rotation and/or a free falling phase, during which the magnitude of the acceleration data is relatively stable and small. Additionally or alternatively the second evaluation logic may comprise body proximity detection means for detecting whether the sensor module is in close proximity to the human body.

21 Claims, 6 Drawing Sheets

FALL DETECTION SYSTEM

FIELD OF THE INVENTION

The invention relates to a fall detection system, for automatically detecting fall incidents of a user.

BACKGROUND OF THE INVENTION

Such automatic fall detection systems are known. They are used to detect fall incidents of a user and report such incidents to a remote care provider who may then take appropriate action. To that end, the detection systems generally comprise a sensor module, to be worn by the user, for collecting movement data of his body, for instance acceleration data. The detection systems further comprise evaluation logic, to detect an impact in the collected movement data. Such impact will occur when the user hits the ground during a fall. However, such impacts may also occur through other events, such as a sudden movement of the user or a collision with his environment. Consequently, the detection of an impact in the acceleration data is not sufficient to positively identify the occurrence of a fall. Therefore, most detection systems are arranged to detect the existence of other pointers, indicative for a fall. It may for instance be verified whether the impact is accompanied by a change in orientation of the user, e.g. a change in posture from standing to lying down. Only in such case the system may raise an alarm to a remote caregiver. Thus, the number of false alarms can be reduced, thereby increasing the reliability of the system and its acceptance by its users.

However, these known fall detection systems may suffer from several drawbacks, as a result whereof false alarms may still occur.

For instance, it frequently occurs that the sensor module itself is dropped from the user's body, for instance during changing clothes. It also occurs that the sensor module has been temporarily placed on a table or the like, and is accidentally knocked there from. In such cases, the known systems will generate an alarm, where they obviously should not.

Other problems may occur when the sensor module is attached to the body in an improper, i.e. disoriented way. This may affect the system's ability to discern changes in the orientation of the user, and may cause the system to draw the wrong conclusions regarding the existence of a fall. More particularly, the system may produce an alarm where there is no fall (a so called false positive), or worse, produce no alarm where there is a fall (a so called false negative). Either situation should be avoided, because it may seriously undermine the confidence in the system.

SUMMARY OF THE INVENTION

Therefore, it is an object of the invention to provide a fall detection system with improved reliability. More particular it is an object of the invention to provide a system wherein the report of false alarms (positives and negatives) is excluded or at least reduced in number.

To that end a fall detection system according to the invention is characterized in that second evaluation logic is provided for verifying that the sensor module is actually worn by the user, at least around the time of the observed impact.

This second evaluation logic may be arranged to scan the acceleration data on the presence of free fall characteristics, i.e. characteristics that are typical for a free falling object, such as one or more full rotations (over more than 360°) or the presence of a free fall phase, just before the impact, during which the magnitude of the acceleration data remains substantially stable and a relatively low value. Investigations have shown that if such free fall characteristics are present, than the observed impact is most likely caused by a fall of the sensor module itself, not a human fall incident.

Additionally or alternatively, the second evaluation logic may be arranged to detect the proximity of the sensor module to the human body. If such proximity cannot be established around the time of the observed impact, than said impact is most likely not caused by a human fall incident.

Thus, thanks to the evaluation logic according to the invention, it can be discerned whether an impact in the acceleration data is caused by a human fall incident or a fall of the sensor module itself. Accordingly false alarms can be prevented. Additionally, if a fall of the sensor module has been detected, the user and/or care provided may be informed that the sensor module is no longer mounted correctly and should be remounted.

According to an advantageous aspect of the invention, if it has been established by the aforementioned evaluation logic that the sensor module is worn by the user, than further evaluation logic may be provided, which is arranged to detect relative changes in the orientation of the sensor module, at least before and after an observed impact in the acceleration data. Thanks to such relative measurement, any change in orientation of the module, and consequently the user, can be detected regardless of the (absolute) orientation of the module just before the impact. The module no longer needs to be attached in one specific orientation. Likewise, the user may fall from any position, i.e. standing, sitting or lying. His initial position (just before the fall) is no longer relevant. If the sensor module undergoes an accidental change in orientation during use, this will not result in an alarm, at least, if this change does not coincide with an observed impact in the acceleration signal. Of course, one or more threshold values may be set to ensure that only orientation changes above a minimum value, e.g. larger than 45 degrees, are taken into consideration when assessing the occurrence of a potential fall incident.

Further advantageous embodiments of a fall detection system according to the present invention are set forth in the dependent claims.

BRIEF DESCRIPTION OF THE DRAWINGS

To explain the invention, exemplary embodiments thereof will hereinafter be described with reference to the accompanying drawings, wherein.

DETAILED DESCRIPTION OF THE EMBODIMENTS

Figure 1:
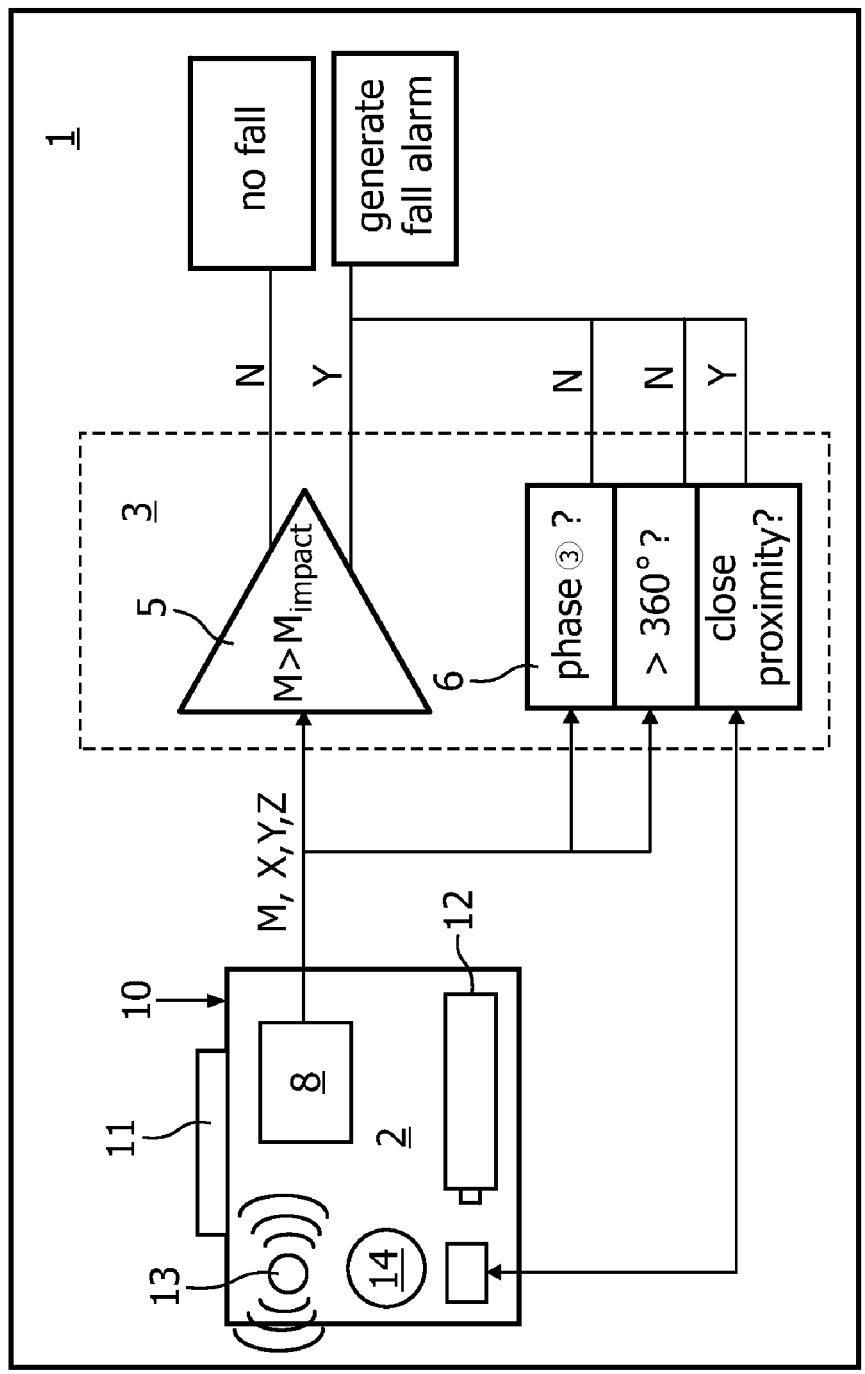
FIG. 1 shows a block diagram of a fall detection system according to the invention.

FIG. 1 shows a block diagram of a fall detection system 1 according to the invention. The fall detections system 1 comprises a sensor module 2, which is to be worn by a user to collect acceleration data X, Y, Z of his body. The detection system 1 furthermore comprises evaluation logic 3, which is arranged to detect whether a human fall incident has occurred. According to the invention, this evaluation logic 3 is divided into first and second evaluation logic 5, 6, wherein the first evaluation logic 5 is arranged to detect a fall incident and the second evaluation logic 6 is arranged to derive whether this fall incident corresponds to a fall of the user or a fall of the sensor module 2.

The sensor module 2 comprises one or more accelerometers 8, preferably arranged to measure acceleration data in three orthogonal directions X, Y and Z. These accelerometer(s) may be accommodated in a housing 10, which may be provided with a clip 11, strap, wristband, necklace or the like attachment means, for easy attachment to the user's body or clothing. Alternatively, the sensor module 2 or detection system 1 as a whole may be an integrated part of the clothing. The housing 10 may furthermore accommodate a power source 12, alarm means 13 such as a buzzer or flashlight, and input means 14 such as one or more push buttons, for instance to manually initiate or annul an alarm.

The first and/or second evaluation logic 5, 6 may be accommodated in the housing 10 of the sensor module 2 or may be accommodated in one or more separate modules, which need not be worn on the user's body. In any case, suitable communication means may be provided to allow data exchange between the said respective modules.

The first evaluation logic 5 is arranged to scan the measured acceleration data X, Y, Z for a potential fall incident. Such fall incident may appear as an impact, i.e. a strong increase in the magnitude M of said acceleration data, during a short period of time, possibly followed by a period of (relative) silence, during which the fallen object (human or sensor module) remains laying down. The first evaluation logic 5 may thus be arranged to monitor the magnitude M of the acceleration signal X, Y, Z and set a flag when a certain pre-set threshold value $M_{impact}$ is exceeded, for example 2.5 g, where g is the gravitational acceleration.

The second evaluation logic 6 is arranged to determine whether the impact is caused through a human fall or a fall of the sensor module 2. This may be done in various ways. For one, the evaluation logic may make use of the differences in fall characteristics of both objects. Generally, the sensor module 2 is likely to feature a free fall whereas the human is not; and the sensor module 2 may undergo one or more full rotations during its fall, whereas the human will not. Furthermore, the evaluation logic may verify whether the sensor module 2 was in close proximity to the user at the time of the observed impact. This too may be verified in various ways. A detailed example of each of the possible evaluation techniques will now be discussed.

It is noted that the reference to 'first' and 'second' evaluation logic in this description does not refer to the order in which this evaluation logic operates. They can operate simultaneously and independent from each other.

Embodiment 1

Detection of a Free Fall Phase

Figure 2:
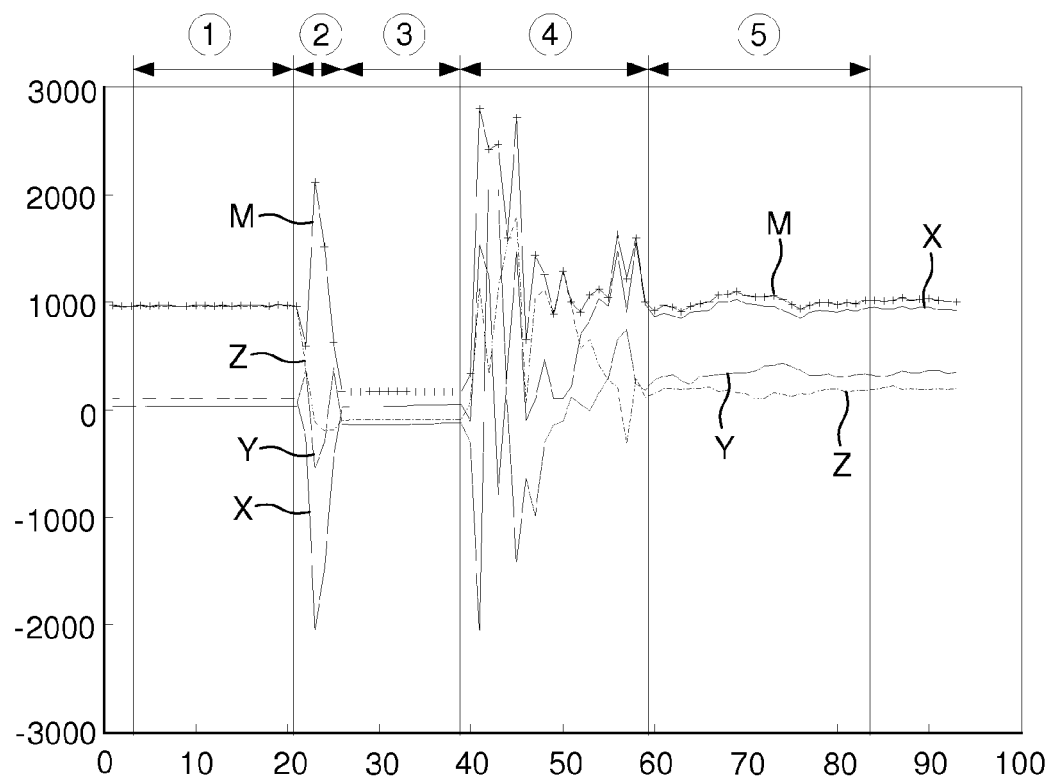
FIG. 2 shows acceleration data of a sensor module falling onto the floor.
Figure 3:
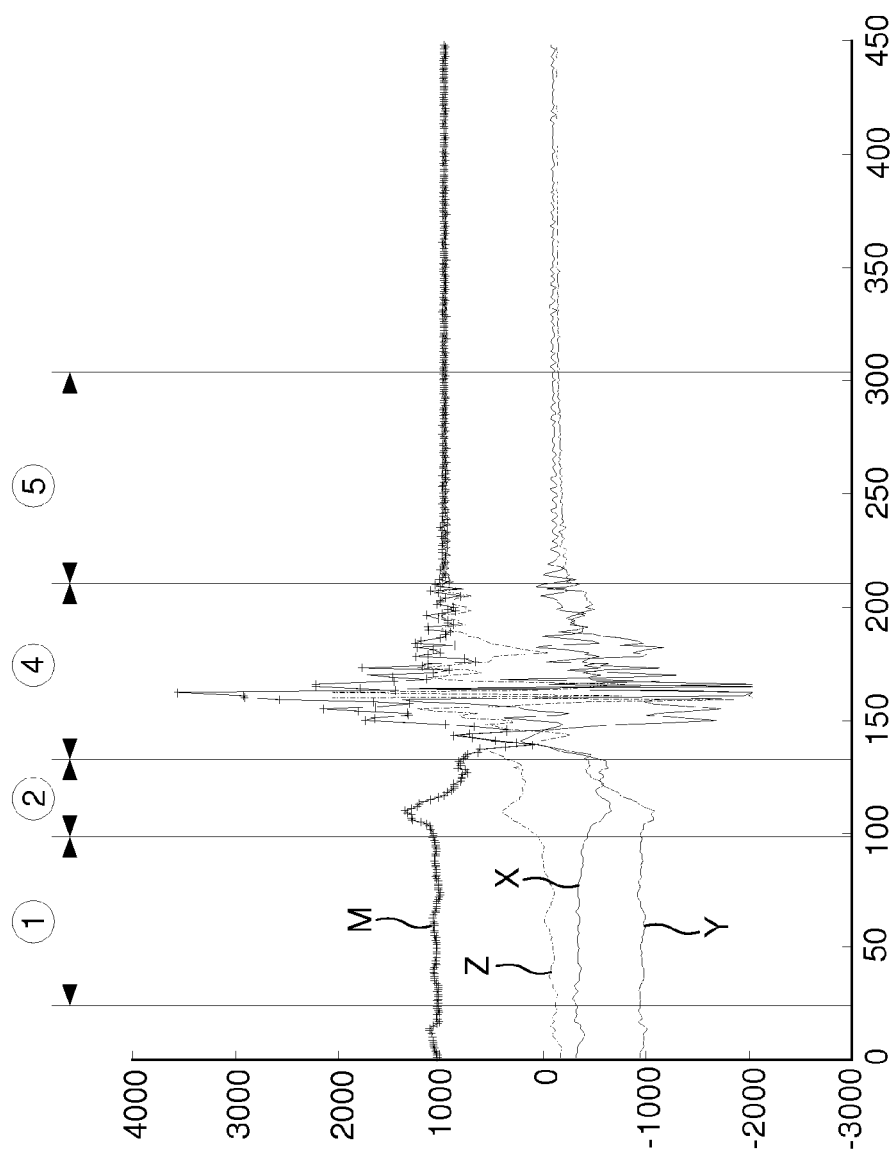
FIG. 3 shows acceleration data of a human falling forward onto the floor.

FIG. 2 represents the acceleration data X, Y, Z as measured during the fall of a sensor module 2, falling from a table onto the floor. FIG. 3 represents the acceleration data X, Y, Z as measured during the fall of a human, falling forward onto the floor. Both FIGS. 2 and 3 furthermore show the magnitude M that may for instance be calculated from:

$$M=\sqrt{X^2+Y^2+Z^2} \quad (1)$$

or from:

$$M=|X|+|Y|+|Z| \quad (2)$$

The acceleration data in FIG. 2 can be divided in five distinct phases, marked ① to ⑤:
- a first phase ①, during which the acceleration data X, Y, Z, M are substantially stable. This corresponds with the sensor module 2 lying still on the table;
- a second phase ②, during which the acceleration data X, Y, Z, M fluctuate in all three directions. This corresponds with the sensor module 2 being pushed over the edge of the table, so as to start its fall;
- a third phase ③, during which the acceleration data X, Y, Z remain substantially stable in all three directions, and the magnitude M is considerably smaller than during the first phase ① wherein the module 2 was still on the table. This corresponds with the sensor module 2 experiencing a free fall;
- a fourth phase ④, during which the acceleration data X, Y, Z, M show large fluctuations. This corresponds with the sensor module 2 hitting the floor and rebounding there from; and
- a fifth phase ⑤, wherein the acceleration data X, Y, Z, M remain substantially stable again. This corresponds with the sensor module 2 lying on the floor, substantially motionless.

The acceleration data X, Y, Z, M in FIG. 3 shows a general resemblance with the data in FIG. 2, with the exception that the third phase ③, i.e. the free fall phase, is missing. The presence, respectively absence of this phase ③ can therefore be used to determine whether a specific acceleration signal is caused by a human fall or a fall of the sensor module 2.

Figure 4:
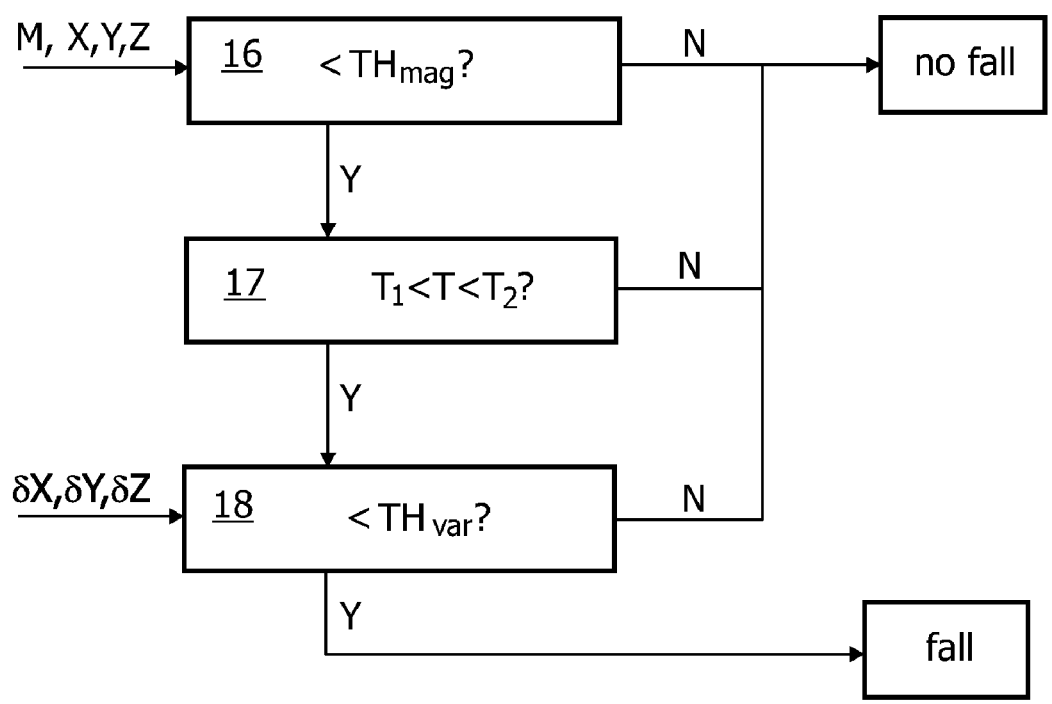
FIG. 4 shows a block diagram of a first embodiment of second evaluation logic according to the invention, arranged to determine the presence or absence of a free fall phase in the acceleration data from FIGS. 2 and 3.

FIG. 4 shows a block diagram of a second evaluation logic 6 for detecting the presence, respectively absence of such third phase ③. The evaluation logic 6 comprises a first block 16 for evaluating whether the magnitude M according to equation (1) falls below a predetermined threshold value ($TH_{mag}$) during a time period (T), a second block 17 for evaluating whether the length of this time period (T) is longer than a minimum length ($T_1$) and shorter than a maximum length ($T_2$) and a third block 18 for evaluating whether within said time period (T) the variance δX, δY, δZ of each of the acceleration components is less than a predetermined threshold value ($TH_{var}$). A free fall phase ③ is detected if the outcome of all three blocks 16, 17, 18 is positive (Y).

The level of the magnitude M in the free fall phase ③ will depend on the magnitude M in the second phase ②, which in turn depends on the initial acceleration of the sensor module 2 when falling from the table. When for instance the sensor module 2 is knocked from the table with considerable force, its initial acceleration, and accordingly its magnitude M in phase ② and phase ③, will be considerably higher than when the sensor module 2 is dropped from the user's hands with substantially no initial acceleration. In the latter case, the magnitude M in phase ③ may be close to zero, whereas in the first case the magnitude M may be much higher. To allow the free fall phase ③ in said first case to be detected, the threshold value $TH_{mag}$ should not be set too low. Preferably, the threshold value $TH_{mag}$ is therefore selected in dependency of the actual measured magnitude in phase ②. $TH_{mag}$ may for instance be defined as one tenth of the maximum magnitude measured during phase ②.

The actual length of the free fall phase ③, i.e. the length of period T, will differ with a height h from which the module falls down according to $h=0.5\,g\,T^2$, with h being the height in meters, g being the gravity acceleration 9.8 m/s² and T being the time in seconds. Thus by selecting a minimum height $h_1$ and a maximum height $h_2$ from which the sensor module may fall in practice, an appropriate minimum length $T_1$ and maximum length $T_2$ may be determined.

The threshold value $TH_{var}$ of the third evaluation block 18 may be determined by experience and can for instance be set at 10.

If with the evaluation logic of FIG. 4 a free fall phase ③ is detected, this information may be used to activate a timer (not shown) for a given pre-set time period $T_{timer}$. If, within this time period $T_{timer}$, the first evaluation logic 5 detects an impact, no fall alarm will be raised.

Embodiment 2

Detection of One or More Full Rotations

Figure 5:
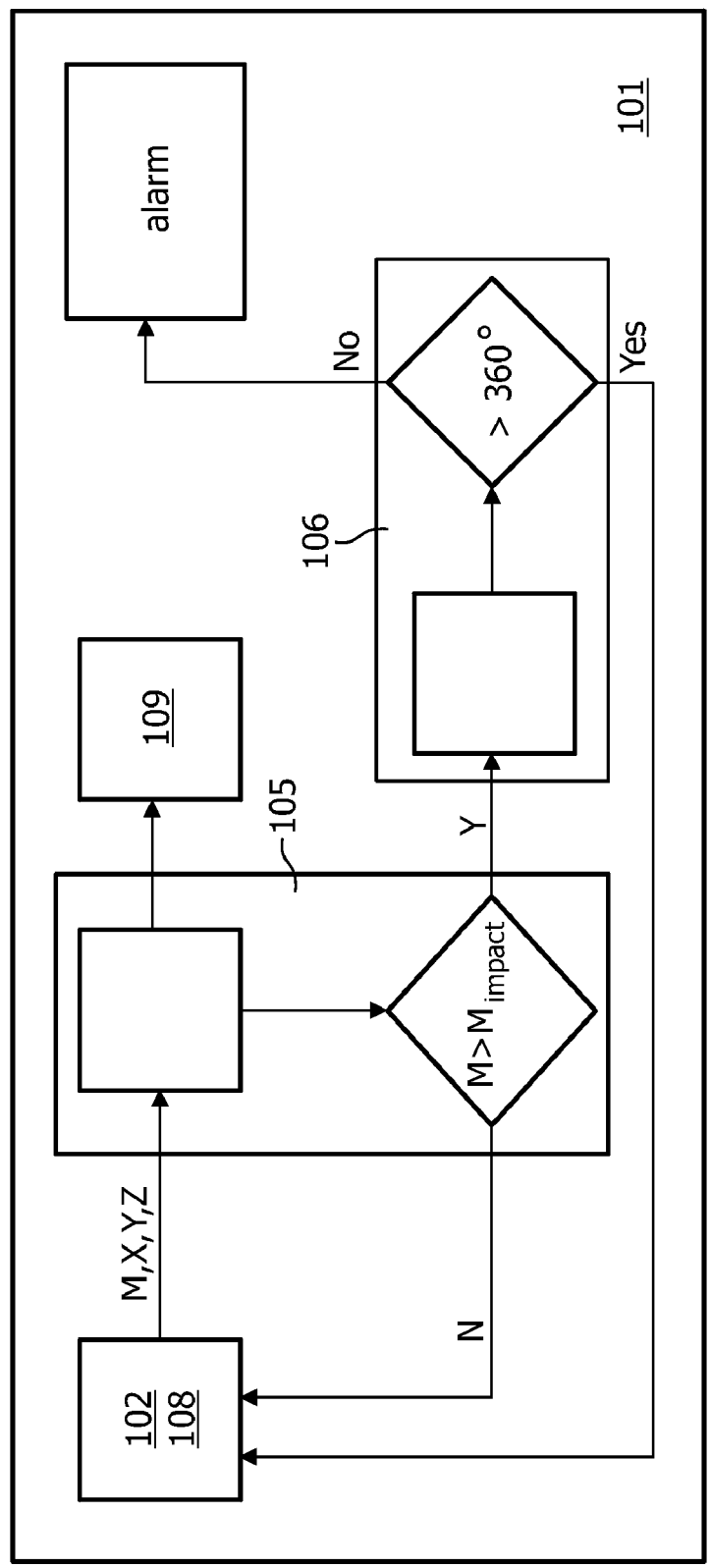
FIG. 5 shows a block diagram of a second embodiment of second evaluation logic according to the invention, arranged to determine the presence or absence of rotations in the acceleration data from FIGS. 2 and 3.

FIG. 5 schematically shows an embodiment of an alternative fall detection system 101 according to the invention, with alternative or additional second evaluation logic 106. Components that are similar to those of embodiment 1 have been identified with similar reference numerals, increased by 100. The second evaluation logic 106 makes use of the insight that small objects, such as a sensor modules 102, tend to make one or more full rotations (i.e. rotate over more than 360 degrees) when falling from a certain height. Persons, on the other hand, will usually not make such full rotations. This insight can therefore be used to distinguish between an accidental drop of the sensor module 102 and a human fall incident.

The detection system 101 according to FIG. 5 comprises a sensor module 102 and first evaluation logic 105 that may be similar to that described in FIG. 1. The sensor module 102 may be provided with one or more angular sensors or gyroscopes for measuring rotations. The second evaluation logic 106 may be arranged to compare the output of said angular sensor or sensors with a certain predetermined threshold value, for instance 360 degrees.

If the first evaluation logic 105 detects an impact and the second evaluation logic 106 detects the presence of one or more full rotations, the detection system 101 may be prevented from generating an alarm, as the observed impact is likely to be caused by a fall of the sensor module 102. If on the other hand, rotations are measured with a rotation angle smaller than 360°, the impact is probably caused by a human fall incident, and a fall alarm may be raised.

According to an alternative embodiment, the second evaluation logic 106 may be arranged to detect the presence of one or more rotations from the acceleration data X, Y, Z measured by a common acceleration sensor 102, i.e. a sensor module with one or more linear acceleration sensors. This may for instance be done as disclosed in U.S. Pat. No. 5,124,938 A, entitled "Gyroless platform stabilization techniques", describing a method to obtain angular acceleration information from accelerometers without using gyroscopes. In such case, no separate angular sensor will be needed, which may save in costs and make the system less complex, more robust.

Embodiment 3

Detection of Close Proximity of Sensor Module and the User's Body

According to yet another embodiment of the invention, false alarms due to accidental falling of the sensor module may be prevented by having the second evaluation logic verify whether the sensor module is in close proximity of the human body (and thus likely to be worn) at the moment of an observed impact. To that end the second evaluation logic may for instance comprise a sensor, which may be accommodated in the sensor module and which is capable of sensing distortion of an electrical field caused by the user's body moving into or out of said field. A suitable sensor is for instance an electrical field sensor, as described in the article "Applying electrical field sensing to Human-Computer interfaces", of authors T. G. Zimmerman, et al., published in IEEE, May 1995.

If, upon the detection of a potential fall incident (by for instance first evaluation logic as described in relation to the previous embodiments), such electrical field sensor can sense distortions, this indicates that the sensor module is in close proximity to the user's body and thus likely to be worn on said body. The fall incident is then likely to be a human fall incident and the detection system may generate an alarm.

Alternatively, close proximity of the sensor module to a user's body may be detected with wireless communication techniques between the sensor module and some other unit, which is securely attached to the user's body. The sensor module and this unit may be provided with a sender and a receiver respectively, or vice versa. Alternatively, the sensor module 2 and the unit may comprise both a sender and a receiver. This sender and receiver are configured such that they can only communicate with each other, when they are at short range from each other, more particularly, when they are coupled to the user's body. Alternatively or additionally the sender and receiver may be configured so as to communicate to each other through body-coupled communication, using the user's body for data transmission. To that end one of the sensor module or the unit may transfer a certain amount of energy to the other through capacitive coupling. Examples of such body-coupled communication are described in the non pre-published patent application WO 2006035351 A2 of applicant, entitled 'System for automatic continuous and reliable electronic patient identification'. The contents of this application are considered to be incorporated herein by reference.

The afore described second evaluation logic 6, 106 may be activated at specific instances, e.g. upon the detection of a potential fall incident by the first evaluation logic 5, 105. Alternatively, said second evaluation logic 6, 106 may be operated continuously or semi-continuously. For instance, the second evaluation logic according to the third embodiment may verify whether the sensor module is in close proximity at regular time intervals. Accordingly, uncontrolled removal of the sensor module can be detected at an early stage. Upon such detection, the user and/or care provider may be informed that the sensor module appears to be removed. In addition, the user may be requested to confirm said observation and/or remount the module within a preset time interval. If within such interval no response is obtained, an alarm may be raised to the care provided. If the proximity of the sensor module is verified regularly, this may also enable a care provider to verify whether the sensor module is properly worn by the user, so as to reassure that a 'no alarm' state corresponds indeed with a 'no alarm' situation.

The above described second evaluation logic according to the invention is not limited to fall detection systems. It may advantageously be applied in other appliances, notably those that are to be worn on a user, without the limiting features of the main claim. Furthermore, two or more of the afore described embodiments of second evaluation logic may be combined, so as to assess even more reliable whether a human fall incident has occurred.

Embodiment 4

Detection of Relative Change in Orientation Sensor Module and/or User

Figure 6:
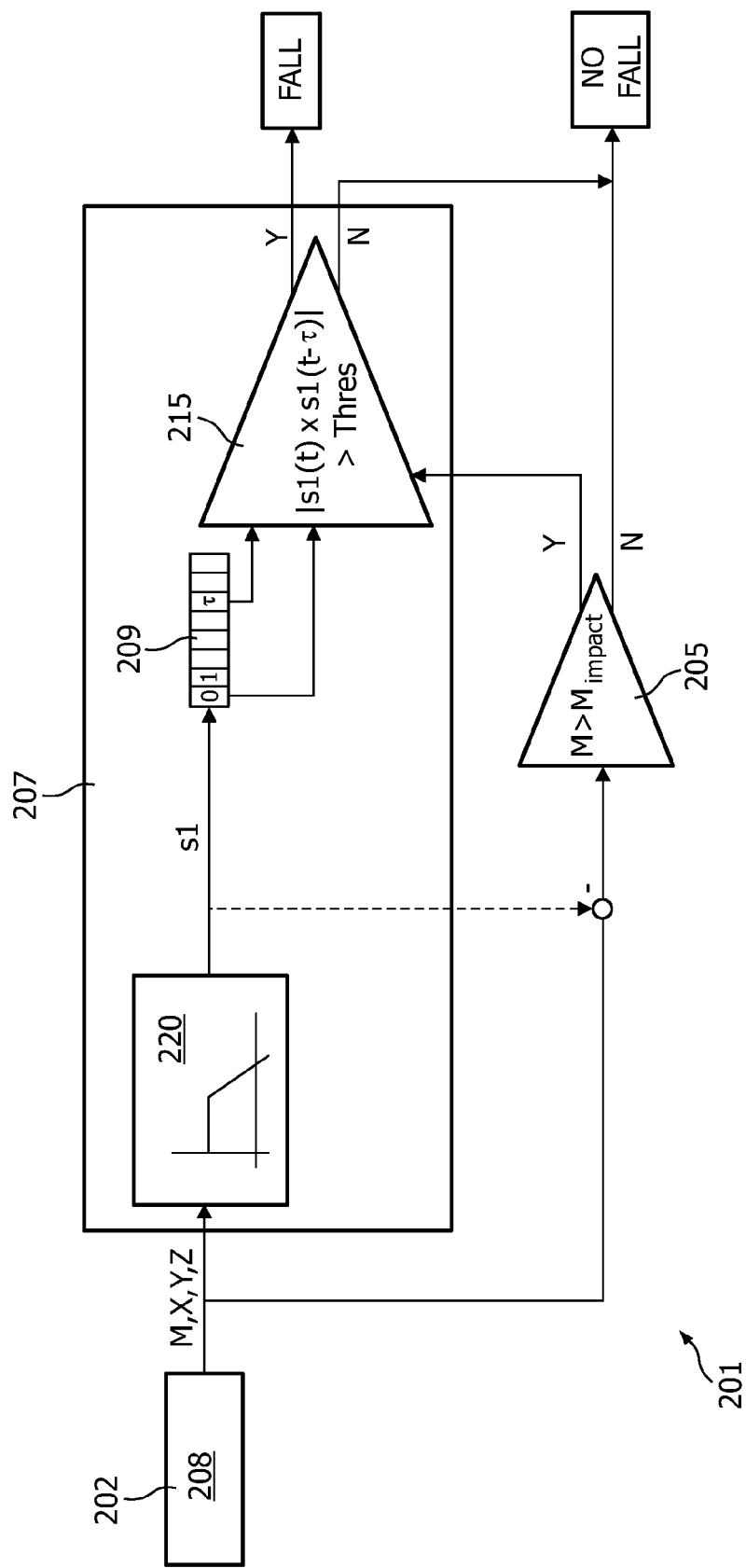
FIG. 6 shows a block diagram of a fourth embodiment of a fall detection system according to the invention, provided with further evaluation logic to detect a relative orientation change of the sensor module.

FIG. 6 schematically shows a further embodiment of a detection system according to the invention provided with improved evaluation logic 207. Components that are similar to those of the previous embodiments have been denoted with similar reference numerals, increased by 200. Once a potential fall incident has been detected, and it has been established that the sensor module 202 is worn by the user (for instance through one of the afore described embodiments), the improved evaluation logic 207 may help to verify whether this fall incident is indeed caused by a fall of the user and not for instance a sudden movement or some other cause. This is done by verifying whether the posture of the user has changed, for instance from standing up to laying down. Conventionally, such change in posture is detected as a deviation in the vertical orientation of the sensor module 202. The sensor module 202 must thereto be attached to the user in a prescribed, vertical orientation and must maintain this orientation during normal activity of the user. If the sensor module 202 is not attached in the right way or shifts during use this may cause false alarms.

The improved evaluation logic 207 according to FIG. 6 overcomes these drawbacks, in that it can detect a change in the user's orientation, regardless the initial orientation of the sensor module 202 (and of the user). The evaluation logic 207 thereto comprises averaging means 220, a memory 209 and a comparator 215.

The working principle of the evaluation logic 207 is based on the insight that changes in the orientation of the sensor module 202 may be detected by averaging the acceleration data X, Y, Z measured by the sensor module 202 over a predetermined time interval. The resulting averaged signal s1 will represent the gravity, since the gravity is the only acceleration that remains constant, at least as long as the sensor module 202 does not change its orientation. The direction given by the X, Y, Z components of the averaged signal s1 therefore represents the direction of the gravity. From this the vertical orientation of the sensor module 202 can be estimated and changes in this vertical orientation will be visible. As a fall is characterized as being accompanied by such change in vertical orientation, averaged signal s1 thus can serve to detect a fall.

The averaging means 220 may for instance comprise a low-pass filter as shown in FIG. 6. This low-pass filter 220 averages the acceleration data X, Y, Z over a time interval $\tau$ that is proportional to the reciprocal of the bandwidth of the filter 220. This averaged signal s1 may subsequently be stored in the memory 209. Upon detection of a potential fall incident (with anyone of the afore described techniques), the comparator 215 compares the direction of the current signal s1($t$) with the direction of an earlier, stored version s1($t-\tau$). To that end, the comparator 215 may compute the vector out product of said signals s1($t$)×s1($t-\tau$), as shown in FIG. 6. If the magnitude of this vector out product exceeds zero or a certain threshold value Thres, a change in orientation is present, and the observed impact may be qualified as an actual fall incident for which an alarm may be raised. The threshold value Thres can be selected to take into account measurement inaccuracies and noise, to avoid that any outcome of the comparator 215 different from zero (caused by such noise) would be interpreted as a change in orientation. The threshold value Thresh may furthermore be increased to a minimum change in orientation that is most likely to occur in case of a fall. It may for instance be derived from experiments that in case of a fall, the change in orientation of the sensor module 202 is usually at least 45 degrees. Changes smaller than 45 degrees are not likely to be caused by a fall. By setting the threshold value Thresh accordingly, false alarms can be even further avoided.

As mentioned above, the time interval t over which the signal s1 is averaged is proportional to the reciprocal of the bandwidth of the low-pass filter 220. For instance, if the filter 220 features a bandwidth of 10 Hz, averaging occurs over a time interval of 100 msec, and if the filter 220 has a bandwidth of 0.1 Hz, averaging occurs over a time interval of 10 seconds. Generally, a long averaging time (small bandwidth) is beneficial for an accurate estimate of the vertical orientation. The drawback, however, is that after an impact a relatively long period of time is needed to determine whether the impact was accompanied by a change in orientation. Generally, strong changes in orientation will be readily detectable, even with short averaging times; small changes in orientation may require longer averaging times. According to an advantageous aspect of the invention this knowledge is used to adjust the bandwidth of the low-pass filter 220 during use, depending on the state of detection. In steady-state, i.e. when there is no potential fall detected (no impact in the acceleration signal X, Y, Z), the bandwidth may be small, resulting in a relatively long averaging time. Upon detection of a potential fall, a broader bandwidth may be adopted, resulting in a shorter averaging time, allowing a first estimate of the current orientation to be obtained relatively fast.

According to a further advantageous aspect of the evaluation logic 207, during steady-state, a trend may be computed by averaging the s1 values stored in the memory 209. Upon the detection of a potential fall, this trend may help to decide whether a small bandwidth will be sufficiently reliable, or whether a large bandwidth seems more appropriate. The stored steady state values of signal $s_1$ may further be used to estimate the variation. This information can then be used to set a realistic threshold Thresh in comparator 215.

The memory 209 may furthermore provide a reference orientation on the basis whereof a change in orientation may be observed after a presumed fall. Since a presumed fall will generally involve strong accelerations, the averaged $s_1$ signal during a presumed fall may be less reliable. Therefore, according to a preferred embodiment, the detection system 201 may compute the differences between the current orientation and those stored in the memory 209 at increasing delay $\tau$, and use this series of differences to refine its decision. Alternatively, it is possible to mark those stored $s_1$ values for which the acceleration signal X, Y, Z has a low energy content. Only these marked s1 values may then be used for deciding whether a change in orientation has occurred.

Furthermore, by monitoring the stored s1 values, aberrations may be detected in otherwise regular patterns. The presence of such aberrations may trigger an alarm or some warning to the user and/or care provider, even without the presence of an impact (potential fall incident) in the acceleration data.

The averaging means 220 can be embodied in different ways. The low-pass filter shown in FIG. 6 may for instance be replaced by an integrator. Alternatively, the averaging means 220 may comprise computation means arranged to compute autocorrelations over a predetermined time window. To that end, the signal $s_1$ may be segmented in windows of length W. The windows may overlap. For example, a first window may range from $s_1[1]$ to $s_1[1+W]$, while a subsequent window may range from $s_1[2]$ to $s_1[2+W]$, i.e. the subsequent window is shifted only one sample period apart. (The square brackets are used to denote a sample period). The length of a window W may for instance be in the order of about 500 ms. In addition, a delayed version of $s_1[t]$ is taken, denoted as $s'_1[t-\tau]$. The delay $\tau$ may for instance be in the order of about 500 ms. $s'_1$ is also windowed with the same window length and the same inter window distance (i.e. the same overlap). The autocorrelation $R_{xy}[w]$ can be computed from following equation:

$$Rxy[w] = \sum_{k=1}^{W} s1[w+k] \cdot s'1[w+k-\tau].$$

The signals $s_1$ and $s'_1$ are vectors. Their product is computed as the inner product. Another definition of their product can be according to the theory of geometric algebra, or Clifford algebra, or according to the theory of quaternions. Furthermore, $R_{xx}$ and $R_{yy}$ can be computed from following equations:

$$Rxx[w] = \sum_{k=1}^{W} s1[w+k] \cdot s1[w+k]$$

$$Ryy[w] = \sum_{k=1}^{W} s'1[w+k-\tau] \cdot s'1[w+k-\tau]$$

$R_{xx}$ and $R_{yy}$ can be used to normalize $R_{xy}$:

$$R'xy[w]=Rxy[w]/\sqrt{Rxx[w]\cdot Ryy[w]}$$

$R'_{xy}$ corresponds to a normalized inner product (also in the case of quaternions) and the change in orientation (rotation angle) can be computed as $$\phi rot[w]=\arccos(R'xy[w])\cdot 180/\pi$$

In case of a fall $\phi_{rot}[w]$ may be large, for instance in the order of about 60 degrees to about 90 degrees, at those instances where w is around the fall incident. $\phi_{rot}[w]$ may be low outside this region, for instance near 0 degrees in case of no movement and $\phi_{rot}[w]$ may be in the order of about 20 degrees to about 50 degrees in case of regular movements such as normal walking. Of course, these values are given for illustrative purposes only. They are not to be construed as limiting.

In all instances, thanks to the averaging means 220 according to the invention, a change in orientation of the sensor module 202 can be detected without said sensor module 202 having to be in a prescribed orientation before the potential fall. It may be attached to the user's body in any arbitrary orientation. Moreover, it is not required for the module 202 to maintain a constant orientation. If during use the orientation of the sensor module changes, and this change is not accompanied by an impact, than no fall alarm will be raised. The new orientation will simply be stored in the memory. Any subsequent orientation check will take this new orientation as reference. Furthermore, there is no restriction to the user's initial posture or orientation at the onset of a fall, i.e. he may have an upright position, a sitting position or even a lying position. The latter situation may for instance arise when a user falls from a bed to the ground. Although in such case, the user's orientation after the fall may be substantially similar to his orientation before the fall, the evaluation logic 207 according to the invention will still be capable of detecting the fall incident if the person during its fall makes a turn, i.e. rolls out of the bed. In such case, the described evaluation logic 207 will measure a rotation change, which then can be used to trigger an appropriate alarm. Thus, with a detection system according to the invention the initial orientation of the sensor module 202 and user no longer matters. Consequently, the sensor module can be mounted in any direction, which enhances its ease of use. Furthermore, reliability of the system is increased, since one source of false alarms (the initial orientation of the user and/or sensor module) is eliminated.

The invention is not in any way limited to the exemplary embodiments presented in the description and drawing. All combinations (of parts) of the embodiments shown and described are explicitly understood to be incorporated within this description and are explicitly understood to fall within the scope of the invention. Moreover, many variations are possible within the scope of the invention, as outlined by the claims.

The invention claimed is:

1. A fall detection system, comprising:
a sensor module to be worn by a user in an arbitrary orientation, for collecting motion data based on the user's motion;
first evaluation logic for identifying a potential fall incident on a basis of an impact observed in said motion data;
second evaluation logic for verifying that the sensor module is actually worn by the user, at least around the time of said impact, the second evaluation logic comprising:
free fall detection logic for evaluating the motion data on characteristics which are typical for a free falling object and arranged to derive whether the potential fall incident corresponds to a fall of the user or a fall of the sensor module independent of the user.

2. The fall detection system according to claim 1, wherein the free fall detection logic is arranged to identify the absence or presence of a free fall phase, wherein during a predetermined time interval preceding the impact, a magnitude of acceleration data is substantially stable and smaller than a preset threshold value.

3. The fall detection system according to claim 2, wherein the preset threshold value is selected as a fraction of the magnitude of the acceleration at the onset of the potential fall incident.

4. The fall detection system according to claim 1, wherein the free fall detection logic is arranged to identify an absence or presence of at least one full rotation.

5. The fall detection system according to claim 1, wherein the free fall detection logic is arranged to identify an absence or presence of at least one full rotation on a basis of linear acceleration data.

6. The fall detection system according to claim 1, wherein the free fall detection logic comprises an angular sensor, for measuring angular motions, in particular angular accelerations.

7. The fall detection system according to claim 1, wherein the second evaluation logic farther comprises body proximity detection logic for detecting whether the sensor module is in close proximity to the user's body.

8. The fall detection system according to claim 7, wherein the body proximity detection logic comprises at least a sender unit and a receiver unit, one being securely attached to the user's body, the other being accommodated in the sensor module, wherein said sender unit and receiver unit only communicate with each other when at a mutual distance which corresponds to or is less than approximately half the user's height.

9. The fail detection system according to claim 7, wherein the body proximity detection logic comprises a sender unit and a receiver unit, which are arranged to communicate to each other through body-coupled communication, wherein the user's body is used for data transmission.

10. The fall detection system according to claim 1, arranged to detect relative changes in orientation of the sensor module.

11. The fall detection system according to claim 10, wherein at least one of the first or second evaluation logics comprises an averaging circuit, for averaging acceleration data obtained from the sensor module, a memory for storing the averaged acceleration data from the averaging circuit, and a comparator for comparing a current direction of the averaged acceleration data with an earlier, stored direction of the averaged acceleration data.

12. The fall detection system according to claim 11, wherein the averaging circuit comprises a low-pass filter, an integrator and/or autocorrelation computation logic.

13. The fall detection system according to claim 12, wherein a time interval over which the averaging circuit averages the acceleration data is adjustable, in accordance with whether or not a potential fall incident has been detected.

14. The fall detection system according to claim 13, wherein the tune interval is adjusted to be relatively long, as long as no potential fall incident has been detected.

15. The fall detection system according to claim 12, wherein the comparator computes a vector product of the current and earlier averaged acceleration data, and computes whether a magnitude of said vector product exceeds a predetermined threshold value.

16. The fall detection system according to claim 7, wherein the body proximity detection logic comprises an electrical field sensor, arranged to measure a distortion of an electrical field, when in close proximity to a user's body.

17. A fall detection system, comprising:
a sensor module configured to be worn by a user for collecting motion data based on motion of the user; and
an evaluation unit, including logic to:
identify the sensor module falling on a basis of said motion data,
differentiate between the user falling while wearing the sensor module and the sensor module falling independent of the user in a free fall based on the motion data, and
generate an alarm in response to the sensor module falling while being worn by the user and generate no alarm in response to the sensor module free falling.

18. The fall detection system according to claim 17, wherein the differentiation between the user failing while wearing the sensor module and the sensor module failing in a free is based upon a full rotation of the sensor module while falling.

19. A fall detection system, comprising:
a sensor module to be worn by a user for collecting motion data based on the user's motion;
evaluation logic identifying a potential fall incident on a basis of an impact observed in said motion data, verifying that the sensor module is currently worn by the user, at least around the time of said impact, and deriving whether the potential fall incident corresponds to a fall of the user or a fall of the sensor module independent of the user, the evaluation logic further including:
an averaging circuit which averages acceleration data obtained from the sensor module over a time interval, the time interval being decreased in response to at least one of detecting a potential fall incident and a change in an orientation of the sensor module.

20. The fall detection system according to claim 19, wherein the sensor module is to be worn by the user at an arbitrary orientation, the evaluation logic further configured to:
estimate an initial relative orientation of the user; and
increase or decrease the time interval over which the averaging circuit averages the acceleration data m response to a strength of a change in the relative orientation of the sensor module.

21. The fall detection system according to claim 20, wherein the time interval is increased in response to a relatively long duration without detecting a potential fall incident, and decreased in response to detecting a potential fall incident.

* * * * *